(12) United States Patent
Gomez

(10) Patent No.: US 7,410,477 B2
(45) Date of Patent: Aug. 12, 2008

(54) SUPRA PUBIC CATHETER

(76) Inventor: Matthew A. Gomez, 2434 Highway 121, Suite 1508, Bedford, TX (US) 76021

( * ) Notice: Subject to any disclaimer, the term of this patent is extended or adjusted under 35 U.S.C. 154(b) by 412 days.

(21) Appl. No.: 11/018,903

(22) Filed: Dec. 21, 2004

(65) Prior Publication Data

US 2006/0135950 A1   Jun. 22, 2006

(51) Int. Cl.
*A61M 29/00* (2006.01)
(52) U.S. Cl. .................................................. 604/96.01
(58) Field of Classification Search ............. 604/96.01, 604/97.01–97.03, 98.01–98.02, 99.01–99.04, 604/101.01–101.05, 103.03–103.09, 104–108, 604/915–921, 500, 506, 507, 509, 510, 502; 606/191–194
See application file for complete search history.

(56) References Cited

U.S. PATENT DOCUMENTS

| | | | |
|---|---|---|---|
| 3,976,080 A | 8/1976 | Bornhorst et al. | |
| 4,143,651 A | 3/1979 | Patel | |
| 4,315,513 A * | 2/1982 | Nawash et al. | 604/537 |
| 4,666,433 A * | 5/1987 | Parks | 604/178 |
| 4,685,901 A * | 8/1987 | Parks | 604/103.03 |
| 4,701,163 A * | 10/1987 | Parks | 604/178 |
| 4,867,745 A | 9/1989 | Patel | |
| 4,888,000 A | 12/1989 | McQuikin et al. | |
| 5,071,405 A * | 12/1991 | Piontek et al. | 604/103.03 |
| 5,458,583 A * | 10/1995 | McNeely et al. | 604/103.13 |
| 5,484,420 A | 1/1996 | Russo | |
| 5,520,636 A | 5/1996 | Korth et al. | |
| 6,039,714 A | 3/2000 | Cracauer et al. | |
| 6,350,255 B1 | 2/2002 | von Dyck | |
| 2003/0009079 A1 | 1/2003 | Beaufore et al. | |

* cited by examiner

*Primary Examiner*—Manuel A Mendez
(74) *Attorney, Agent, or Firm*—Eric Karich

(57) ABSTRACT

A device for retaining a supra pubic catheter having a moveable retainer axially moveable along the catheter.

4 Claims, 2 Drawing Sheets

SUPRA PUBIC CATHETER

FIELD OF INVENTION

This invention relates to a device for retaining a supra pubic catheter and particularly relates to a supra pubic catheter with a moveable device along a catheter for improved sealing characteristics as well as the use of the system and method relating thereto.

BACKGROUND TO THE INVENTION

Whether due to disease, stroke or Alzheimer's, a percentage of the population cannot urinate through their urethras. Such patients may be catheterized with a urinary catheter where the catheter is passed through the urethral of the patient until a distal end of the catheter is located in the patient's bladder. Thereafter, an expandable balloon is expanded to lodge the distal end of the catheter in the bladder. During catheterization, with a urinary catheter, urine drains from the bladder through the catheter, and through a drainage tube attached to a proximal end of the catheter to a drainage bag for collection therein.

Another system comprises the use of supra pubic catheters where the catheter passes through the abdomen wall of the patient until the distal end of the catheter is located in the bladder. This technique bypasses the urethra all together, and the bladder is connected to the outside of the body in the pelvic region. A surgical procedure is conducted where a stoma tunnel made of body tissue leads from the bladder to the outside of the abdomen.

Such supra pubic catheters have been used to drain urine by placing a urethral catheter through the tunnel or stoma. A balloon at one end, namely the distal end, is inflated with sterile water or saline inside the patient's bladder in order to keep the catheter in place. Thus, fluid from the bladder exits through the hollow passageway of the catheter to the exterior of the patient's body. Examples of such prior art devices and procedures are disclosed in U.S. Publication No. U.S. 2003/0009079, U.S. Pat. No. 4,867,745 and U.S. Pat. No. 4,143,651.

Moreover, U.S. Pat. No. 4,888,000 discloses a supra pubic catheter inserted by way of a cannula which is positioned using a trocar, the trocar being withdrawn to leave the cannula in position through the wall of the bladder, allowing passage of the supra pubic catheter, the cannula being provided with means for subsequent removal from the catheter.

Also, U.S. Pat. No. 5,520,636 teaches a device for flushing the urinary bladder.

Furthermore, U.S. Pat. No. 6,350,255 illustrates a pad for use with a continent ostomy port which includes a body portion having a internal wall defining an aperture appropriately sized placed around a stoma, the body portion of the pad being sized and shaped for placement against the user's skin beneath a face place of an ostomy port. The pad is formed of a soft, flexible material to thereby cushion and protect the skin from contact with the ostomy port face plate.

One of the difficulties with the current technique and prior art devices resides in the fact that the inflated balloon does not stay in place, either due to patient's movement or the play in migration inwards and outwards of the catheter which breaks the seal. Furthermore, the weight of the saline filled balloon may cause leaking of air and fluid. Ideally, the fluid or urine drains from the bladder with the use of the relatively higher pressure in the bladder when compared to the atmosphere pressure in the drainage bag or the like, as well as due to the gravity. In those circumstances, where there is no seal, drainage relies on gravity alone.

In addition, when a good seal is not maintained, urinary leakage occurs. The patient is wet and in addition the weight of the patient in bed and the pressure on the skin increases a patient's risk of infection, skin breakdown and formation of decubitus ulcers. There is a general concern for decubitus ulcers in the sacrum and bilateral hips which manifest itself as Ishial tuberosities. If a patient already has decubitus ulcers in these areas with urine leakage on such dressing affects the effectiveness of the dressing and the medication under the dressing, which ultimately leads to various complications.

Moreover, leakage of air and fluid around catheter provides an avenue for infection. If air and or fluid can leak out, organisms can be introduced through this access. The catheter outside the skin and any organisms on this catheter will be deposited in the bladder by the migration and play of the catheter.

Moreover, it has been documented that, without properly securing the urethral catheter, the stoma over time, becomes larger and eventually causing insertion of a larger catheter. This causes the patient more trauma and discomfort. Much of the existing difficulties may stem from the fact that urethral catheters are used in supra pubic catheter applications.

Accordingly, there is a need for improved apparatus and method as well as system for a supra public catheter.

Retention bolsters for gastrostomy and other ostomy tubes have been disclosed as illustrated in the U.S. Pat. No. 6,039,714. Moreover, retention bolster for percutaneous catheters which have a convexly curved exterior surface which contacts the epidermal surface of the patient are shown on U.S. Pat. No. 5,484,420.

Finally, U.S. Pat. No. 3,976,080 teaches an endotracheal tube holder.

There is a need for an improved apparatus, method and system for supra pubic catheters.

SUMMARY OF THE INVENTION

It is an aspect of this invention to provide a device for retaining a supra pubic catheter having an expansible balloon at one end of the catheter for maintaining the catheter in place and a slidable flange received by the other end of the catheter.

It is another aspect of this invention to provide the combination of a supra pubic catheter adapted to be placed through a stoma, the catheter having one end with an inflatable balloon adapted to be inflated inside the bladder, and a device axially moveable along the catheter towards the balloon.

There is another aspect of this invention to provide a method of treating a bladder by use of supra pubic catheter comprising: placing a supra pubic catheter through a stoma in an abdomen of a patient into the bladder, inflating a balloon disposed at one end of the catheter in the bladder to maintain one end of the catheter and said bladder, moving a retainer along the catheter towards the abdomen to draw said catheter balloon against said bladder.

It is a further aspect of this invention to provide for the use of a supra pubic catheter for a bladder comprising: inserting a supra pubic catheter through a stomal tunnel in an abdomen of a patient into the patient's bladder, inflating a balloon disposed at one end of the catheter in the bladder, moving the catheter towards the abdomen to draw said catheter balloon against the bladder.

These are the objectives and features of the invention should all be described in relation to the following drawing:

DESCRIPTION OF THE INVENTION

Figure 1:
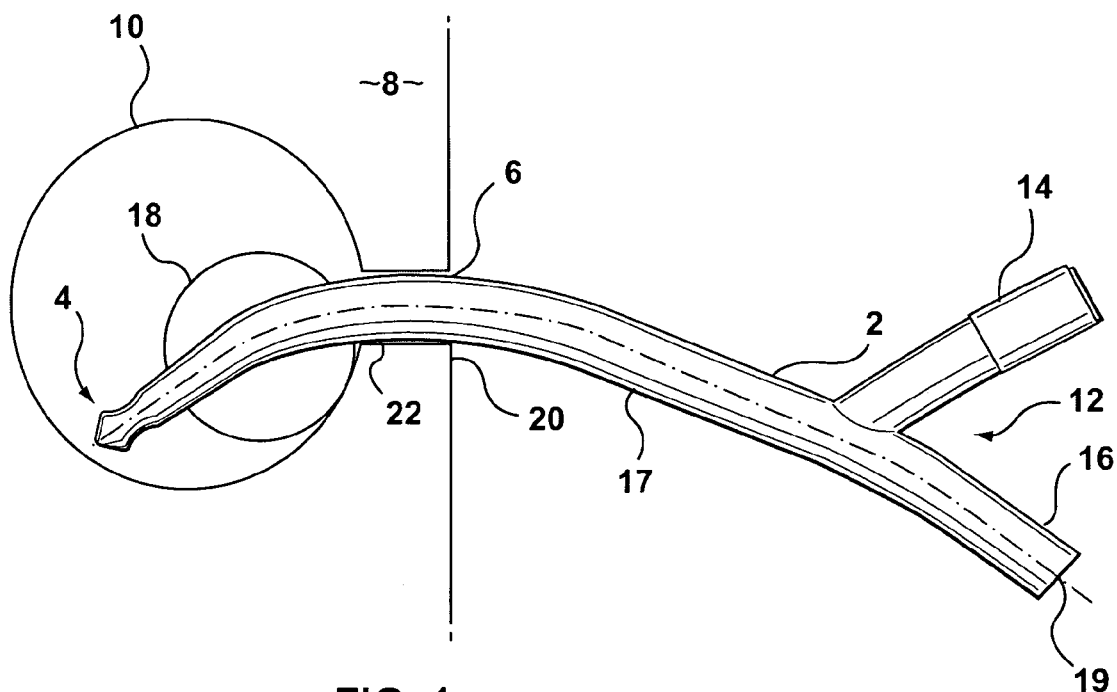
FIG. 1 illustrates a prior art urethral or urinary catheter.

In the description which follows, like parts are marked throughout the specification and the drawings with the same respective reference numerals. The drawings are not necessarily to scale and in some instances proportions may have been exaggerated in order to more clearly depict certain features of the invention.

FIG. 1 illustrates a prior art urethral or urinary catheter 2 which has one end of distal end 4 adapted to be placed through a stoma 6 of a body 8 towards a bladder 10. The stomal tunnel is produced by a trocar under sterile conditions. The catheter 2 has a "Y" branch 12 where one of the branches 14 is adapted for inserting saline solution through the catheter so as to inflate the balloon 18 in a manner well known to those persons' skill and art.

Moreover, the abdomen 8 generally comprises of the public wall.

In the system illustrated in FIG. 1, the catheter 2 has one end or distal end 4 inserted directly into the bladder through the supra pubic area. The balloon 18 of the catheter 2 is then inflated within the bladder, by introduction of saline solution through branch 14 by way of example, and then pulled snuggly to occlude the opening 20 from the bladder to the stomal tunnel 22. In particular the catheter has two coaxial passages one that communicates with the balloon 44 and branch 50, and the other that communicates with the holes 43 at the distal end to drain urine through end 19. One of the problems encountered in the prior art is that the balloon moves (hence the seal is broken) due to the flexibility of the rubber or silicone catheter, the weight of the fluid filled balloon 18, along with any slight movement of the patient or catheter.

Figure 2:
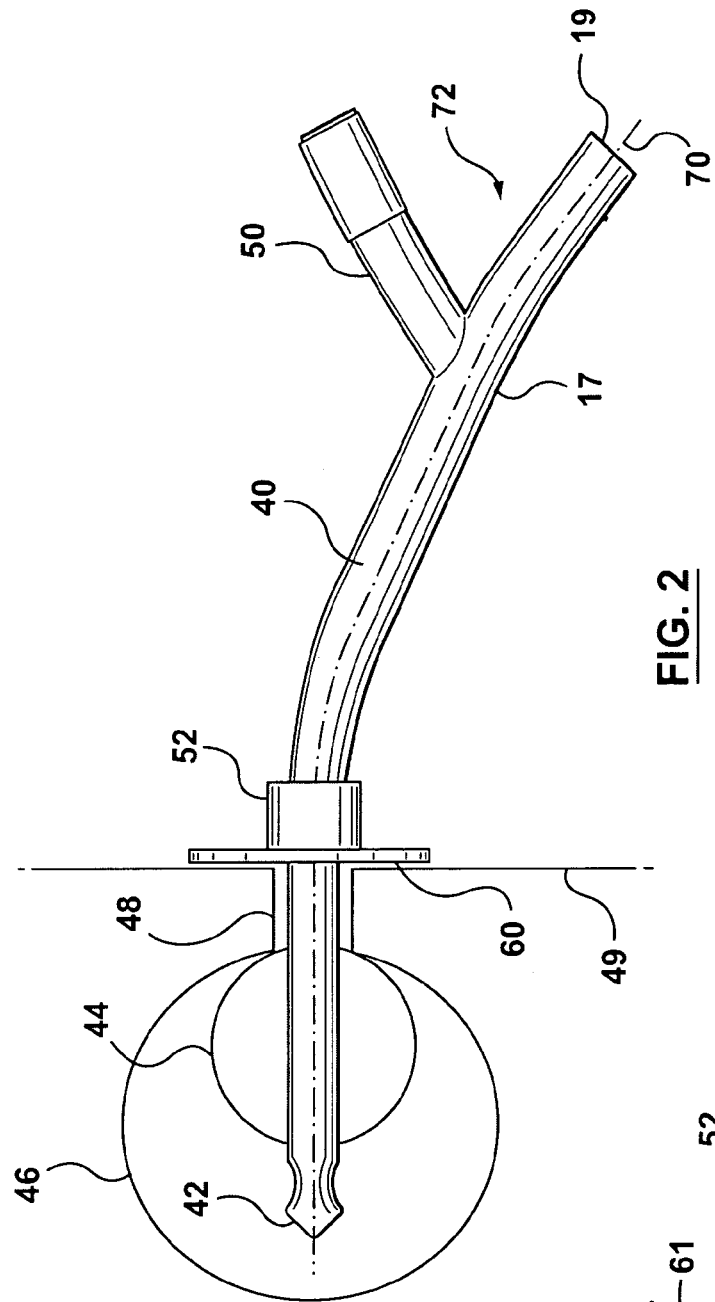
FIG. 2 illustrates the supra pubic catheter disclosing the invention.
Figure 4:
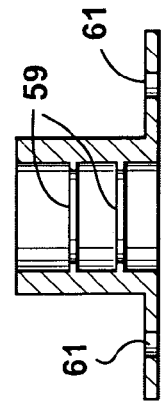
FIG. 4 is a cross sectional view along the lines of 4-4 of FIG. 3.

FIG. 2 illustrates and describes therein a catheter 40 having at its distal end 42 an inflated balloon 44. In particular, the catheter 40 is inserted directly into the bladder 46 through the supra pubic area through a stomal tunnel 48 produced by the surgical use of the trocar (not shown) in the abdomen or pelvic wall. The balloon 44 on the catheter 40 is then inflated within the bladder by means of the "Y" branch 50 in a manner well known to those persons skill in the art. Upon inflating the balloon 44, the catheter is then pulled snuggly to occlude the opening from the bladder 46 to the stomal tunnel 48. FIG. 2 also discloses that one of the branches 16 communicates with the remainder of the catheter to present a passage way 17 which permits voiding of urine through the catheter out the exit 19.

Figure 3:
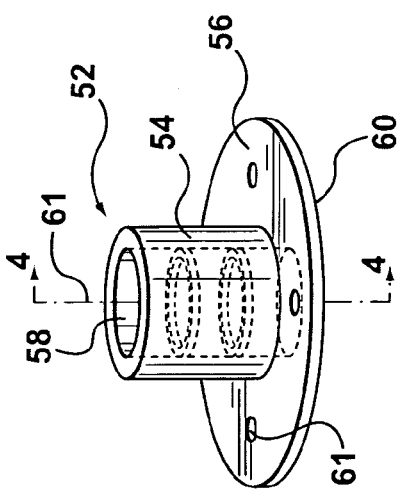
FIG. 3 illustrates the retainer.

A flange 52 is disposed along the catheter. The flange, more particularly described in FIG. 3 consists of a sleeve and hollow cylindrical portion 54 having a hole or bore 58 there through. Cylindrical portion 54 is symmetrical about axis 60. The retainer device 52 also comprises the radially extending flange portion 56.

In particular, the inner diameter of the hole 58 is sized so as to be slidably moveable along the longitunal axis 70 of catheter 40 in the region between the pelvic wall 49 and the proximal end 72 of the catheter 40, yet frictionally engage the outer diameter of catheter 40 when contacting the epidermal skin layer of the patient.

More particularly in one embodiment shown the hole 58 has capturing means 59 disposed interiorially of the hole 58. In particular the capturing means comprise a plurality of internally disposed projections or rings 59. Therefore the catheter 40 which is comprised of stretchable material is adapted to be received co axially within hole 58 and ride past the rings 59. Once the retaining device is placed in the desired position the flexible nature of the retainer and cather relaxes and the rings 59 assist in retaining the retainer 52 in the desired position on the catheter.

The retainer 52 also includes one wall 60 which is adapted to contact the pelvic wall 49. In the embodiment shown in FIGS. 2 and 3, the catheter 40 is inserted directly into the bladder 46 through the supra pubic area through stomal tunnel 48. The balloon 44 and the catheter 40 is inflated within the bladder 46 and pulled snuggly to occlude the opening from the bladder 46 to the stomal tunnel 48. The retainer 52 is then slidably disposed along the axial length 70 (exterior of the body of the patient) towards the balloon 44 so as to secure the balloon 44 under slight tension in its ideal location thereby creating a substantially closed or sealed system. In other words the length of catheter between the balloon 44 and the disc 52 contacting the exterior skin is under slight tension.

The system described herein comprises:

(a) Placing a supra pubic catheter through a stomal tunnel from the outside skin of the abdomen of the patient to the bladder;

(b) Inflating a balloon disposed at one end of the catheter, in said bladder to maintain said one end of the catheter in said bladder;

(c) Moving a retainer along the catheter towards the abdomen to draw said catheter balloon against the bladder.

With the system described herein, the retainer 52 holds the balloon over the inner, namely the bladder side opening to the stomal tunnel thereby providing a chance from the mucosa in the tunnel to dry and crust thus permitting healing to take place. Thereby, the opportunity for infection is minimized thus improving the patient comfort and providing the least disruption to the body image.

The system described herein provides the following advantages:

1. Reduces leakage from the stoma opening, due to a seal created from the flange and balloon.
2. The catheter stays in place, as the flange secures the catheter from any type of movement within the stoma.
3. The skin breakdown is significantly reduced, because the leakage is stopped since the stoma is sealed by the balloon secured in place by the retaining device.
4. Infection to the stoma area is reduced when the seal is create with the retainer, inhibiting any foreign matter from entering the stoma tunnel, thereby lowering the incident of Urosepsis and sepsis with air and fluid.
5. With a seal, the stoma has a chance to heal; since air contacts the normal mucosa in the stomal tunnel thus allowing granulation and healing.
6. Stoma enlargement is minimized.
7. Patient comfort and body image is significantly improved, because the seal keeps the area from leaking, giving the patient peace of mind that they will not have leakage in public.
8. Physical activity of the patient is significantly improved since the seal keeps the area from leaking which intern allows the patient the freedom to participate in activities they normally would not with previously used catheters.

Moreover, the catheter can be comprised of plastic such as bio compatible polymers, including silicone, rubber, silicone elastomers, polyurethane, silicone copolymers, polypropylene and/or similar materials or combination thereof typically used in the art.

The flange can be comprised of the similar material.

Furthermore the invention comprises the kit which includes the supra pubic catheter and retainer.

Various embodiments of the invention have now been described in detail. Since changes in and/or additions to the above-described best mode may be made without departing from the nature, spirit or scope of the invention, the invention is not to be limited to said details.

The invention claimed is:

1. A method of inserting a supra pubic catheter, the method comprising the steps of:
   providing the supra pubic catheter having a proximal end and a distal end, the distal end having an inflatable balloon, and the proximal end having a retainer that frictionally engages the catheter;
   surgically creating a stomal tunnel in a pelvic wall through to the bladder;
   inserting the distal end of the catheter having the balloon through the stomal tunnel and into the bladder;
   inflating the balloon such that the distal end of the catheter is maintained in the bladder; and
   sliding the retainer along the catheter towards the pelvic wall such that the balloon is secured against the bladder to prevent leakage within the stomal tunnel and movement of the balloon relative to the bladder.

2. The method of claim 1, wherein the retainer includes a hole for co-axially receiving the catheter.

3. The method of claim 2, wherein the retainer includes a plurality of internal rings in the hole such that the rings aid in the retainer frictionally engaging the catheter.

4. The method of claim 1, wherein the retainer includes a wall adapted to abut the pelvic wall.

* * * * *